United States Patent
Zambias et al.

(10) Patent No.: US 6,426,006 B1
(45) Date of Patent: Jul. 30, 2002

(54) AUTOMATED ON-LINE EVAPORATING LIGHT SCATTERING DETECTION TO QUANTIFY ISOLATED FLUID SAMPLE COMPOUNDS IN MICROTITER PLATE FORMAT

(75) Inventors: Robert A. Zambias, San Diego; Daniel B. Kassel, Del Mar, both of CA (US)

(73) Assignee: Deltagen Research Laboratories, L.L.C., San Diego, CA (US)

( * ) Notice: Subject to any disclaimer, the term of this patent is extended or adjusted under 35 U.S.C. 154(b) by 48 days.

(21) Appl. No.: 09/710,363

(22) Filed: Nov. 8, 2000

Related U.S. Application Data

(62) Division of application No. 09/415,541, filed on Oct. 8, 1999, now Pat. No. 6,210,571, which is a division of application No. 09/219,083, filed on Dec. 22, 1998, now Pat. No. 6,077,438.

(51) Int. Cl.[7] .............................................. B01D 15/08
(52) U.S. Cl. .................... 210/659; 210/656; 210/198.2; 73/61.52; 436/161
(58) Field of Search ................................. 210/635, 656, 210/659, 198.2; 73/61.52, 61.58; 422/70; 436/161

(56) References Cited

U.S. PATENT DOCUMENTS

| | | | |
|---|---|---|---|
| 4,840,730 A | 6/1989 | Saxena | 20/659 |
| 5,234,586 A | 8/1993 | Afeyan et al. | 210/198.2 |
| 5,670,054 A | 9/1997 | Bibbey et al. | 210/659 |
| 5,766,481 A | 6/1998 | Zambias et al. | 210/659 |
| 5,938,932 A | 8/1999 | Connelly et al. | 210/198.2 |

FOREIGN PATENT DOCUMENTS

| | | | |
|---|---|---|---|
| WO | WO 96/40398 | 12/1996 | 210/659 |
| WO | WO 99/25452 | 5/1999 | 210/659 |

OTHER PUBLICATIONS

Roda, Aldo et al., High–Performance Liquid Chromatographic–Electrospray Mass Spectrometric Analysis of Bile Acids in Biological Fluids, *Journal of Chromatography B*, 665 (1995) pp. 281–294.

Garr, PhD, Cheryl et al., The Use of Evaporative Light Scattering in Quality Control of Combinatorial Libraries, MDS Panlabs, Inc., Apr. 28–29, 1997, pp. 1–18.

*Primary Examiner*—Ernest G. Therkorn
(74) *Attorney, Agent, or Firm*—Townsend and Townsend and Crew LLP

(57) ABSTRACT

Single pass methods and systems for measuring the total masses of individual compounds present in fluid samples in real time, and particularly for fluid samples prepared in microtiter plate format are provided. Individual compounds are isolated by fluid separation column (14). Portions of the individual compounds isolated by column (14) are analyzed by mass spectrometer (16), which determines their concentration on the basis of their molecular weights, and an evaporative light scattering detector (24), (which determines the total masses of each of the isolated compounds passing therethrough). Total collected masses of the individual compounds are calculated by determining the amount and portion of the isolated compounds diverted into evaporative light scattering detector (24) during a period of fraction collection.

10 Claims, 4 Drawing Sheets

AUTOMATED ON-LINE EVAPORATING LIGHT SCATTERING DETECTION TO QUANTIFY ISOLATED FLUID SAMPLE COMPOUNDS IN MICROTITER PLATE FORMAT

CROSS-REFERENCES TO RELATED APPLICATION(S)

The present application is a divisional patent application of U.S. patent application Ser. No. 09/415,541, filed Oct. 8, 1999, now U.S. Pat. No. 6,210,571 and divisional patent application which claims the benefit and priority of U.S. patent application Ser. No. 09/219,083 filed Dec. 22, 1998, now U.S. Pat. No. 6,077,438, the full disclosure of which is incorporated herein by reference for all purposes.

TECHNICAL FIELD

The present invention relates to quantifying (or measuring the amounts) of reaction compounds which are fraction collected in microtiter plate format.

BACKGROUND OF THE INVENTION

Systems exist for the parallel synthesis of various chemical compounds in microtiter plate format. Accordingly, many liquid handling systems have been developed for automated parallel synthesis in conjunction with such microtiter plate formats. High throughput liquid chromatography/mass spectrometry systems capable of isolating compounds on the basis of their molecular weight have also been developed. However, a system for easily and efficiently determining the total collected masses of compounds which are fraction collected in microtiter plate format has proven elusive.

In general, existing high throughput liquid chromatography/mass spectrometry systems isolate compounds by fractionation into fraction collector tubes which are individually removable from a rack. Numerous problems exist when attempting to quantify the total mass of each of the compounds collected in the various fraction collector tubes. First, each tube in the rack needs to be individually removed, weighed and its weight recorded. The compounds are then fraction collected into the individual tubes in the rack. Subsequent to fraction collection, the tubes are removed one after another from the rack and are placed in a device which concentrates them down by driving the contents of the tube. After the contents of the tube have been concentrated down by drying, the dried tubes are individually re-weighed and the net weight of each sample in the fraction collection tubes is then determined by comparing the initial weight of the empty tube with the weight of the tube with the dried compound therein. The weight information so determined allows the compounds to be redissolved with a volatile solvent to a desired set point molarity. The tubes are then placed into a rack and an aliquot is delivered into a microtiter plate for use in a biological assay.

In high throughput synthesis operations, the number of samples can be quite large so the operation of separately weighing, re-weighing, tracking, and labeling a very large number of fraction collector tubes becomes quite cumbersome. Moreover, when weighing and re-weighing relatively small volume fluid samples, inaccuracies in the weight of the tubes themselves may account for larger weight differences than the weight of the compound fraction collected therein. As such, significant errors can be introduced to the net weight of each collected compound, and its final concentration upon dissolution. In addition, special devices such as racks and an apparatus for concentrating down fluid samples have to be used with the dried down products later having to be reformatted into a microtiter plate format.

SUMMARY OF THE INVENTION

The present invention provides methods and systems for measuring the total masses of individual compounds present in fluid samples, and is particularly well adapted for use with fluid samples prepared in microtiter plate format. In a preferred aspect, the individual compounds are isolated by fluid separation systems including high performance liquid chromatography columns and supercritical fluid columns. Small portions of the individual compounds isolated by fluid separation are then analyzed by a mass spectrometer, (which determines the compound molecular weight), and by an evaporative light scattering detector, (which determines the total masses of each of the isolated compounds passing therethrough). The present invention provides a single pass system which measures the masses of the individual compounds diverted into fraction collectors in real-time, as follows.

The signal generated by the mass spectrometer is used to determine the interval of time during which fraction collection is to be carried out. The signal generated by the evaporative light scattering detector is used to determine the total amount of mass diverted therethrough during the interval of time during which fraction collection is carried out. By knowing the portion of fluid sample diverted into the evaporative light scattering detector, (relative to the portion of fluid sample which is directed to fraction collection), it is then possible to calculate the total masses of each of the individual isolated compounds as they are fraction collected.

By selecting intervals of time for fraction collection on the basis of when a desired compound is present in sufficient concentration, (as indicated by the signal strength from the mass spectrometer), the individual isolated compounds can be purified as they are fraction collected. Thus, an advantage of the present invention is that, during only a single pass through the system, each fluid sample is partitioned into isolated compounds which are individually weighed in real time as they pass into fraction collectors.

An additional advantage of the present invention is that microtiter plate formats can be used both for sample preparation reactions and for fraction collection of the individual compounds present in such samples. Accordingly, the present invention provides a single-pass system for the synthesis, isolation, weight measurement, and delivery of compounds in microtiter plate formats.

Another advantage of the present invention is that it is able to determine the total mass of the individual isolated compounds present in microtiter plate fluid samples at the same time that these individual compounds are being fraction collected in microtiter plate format. As such, only a single pass of a fluid sample through the system is required to isolate the individual compounds in the fluid sample, to fraction collect the individual isolated compounds and determine the total collected masses of these isolated compounds.

Therefore, an additional important advantage of the present microtiter plate format single pass system is that it completely avoids individually removable fraction collection tubes. Accordingly, it is not necessary to individually weigh individual tubes containing fractionated fluid samples. Consequently, it is not necessary to separately track and label such tubes or to transfer individual tubes between various liquid handling, concentrator and fraction collection devices. As such, the problem of individual tubes being misplaced or transposed and the amount of time involved with transferring individual collection tubes is completely avoided. Thus, another advantage of the present invention is that by using a high density microtiter plate format, the present invention reduces the actual amount of material which needs to be synthesized, (as compared to existing non-microtiter plate format systems), thereby resulting in cost savings through the reduced costs of synthetic chemicals. By using a small volume microtiter system, solvent consumption is reduced. Moreover, being a small volume system, significant reduction in the disposal of waste streams is achieved.

An additional advantage of the present small volume microtiter plate format is that, in preferred aspects, more difficult chromatographic separations can be achieved with the resolution of present invention's preparatory or semi-preparatory chromatographic column where the resolution approaches that of a conventional smaller analytical chromatographic column.

Existing systems which remove and re-weigh fraction collection tubes individually can not be operated with the small fluid sample volumes of the present microtiter based system since inaccuracies in the weight of the tube itself may account for larger weight differences than the weight of the collected fluid sample therein. As such, significant errors can be introduced to the net weight of each product. The present invention completely avoids this problem.

In the present invention, a plurality of fluid samples are first provided in a standard microtiter plate format. An autosampler is then used to sequentially load the fluid samples onto a fluid separation system which preferably comprises a preparatory or semi-preparatory high performance liquid chromatography (HPLC) column or a supercritical fluid chromatography (SFC) column, which separates the components in each fluid sample such that individual compounds are isolated by sequential elution from the fluid column. Keeping within the scope of the present invention, however, alternate systems which facilitate fluid based separation can be used.

A very small portion, (typically on the order of 1%), of the sequentially eluted isolated compounds in the separated fluid sample are diverted into a mass spectrometer which determines the molecular weight of the individual isolated compounds passing therethrough. The signal generated by the mass spectrometer will correspond to the molecular weight of the compound passing therethrough such that fraction collection can be performed when a desired isolated compound is present in a desired concentration. As such, the output signal of the mass spectrometer can be used to signal the interval of time during which fraction collection is to be performed.

In addition, a very small portion, (typically on the order of 1%), of the sequentially eluted isolated compounds in the fluid sample are diverted into an evaporative light scattering detector. The evaporative light scattering detector generates a chromatographic signal of the sequentially eluted isolated compounds which is proportional to the total masses of the various compounds passing therethrough. An advantage of evaporative light scattering detection is that it is mass dependent and will tend to be generally uniform over a wide range of different chemical structures. Accordingly, a single calibration curve can be generated between masses passing through the evaporative light scattering detector and its signal output.

As stated, the mass spectrometer is used to selectively signal fraction collection of the compounds isolated in the fluid sample on the basis of their molecular weights and the light scattering detector signal is used to determine the actual total masses of the isolated compounds which are collected into the fraction collection microtiter plates.

In particular, the portion of each isolated compound diverted into the light scattering detector, (as compared to the remainder which is directed either to fraction collection or to waste), will be the same for all isolated compounds and will be determined by the dimensions of the splitter device used to divert a portion of the fluid sample into the light scattering detector. However, the portion of each isolated compound which is fraction collected as opposed to being diverted to waste will vary for different compounds, being dependent upon the portion of time during which fraction collection is carried out. The portion of time during which fraction collection is carried out will in turn depend upon the amount of time during which the compound is eluted at a sufficient purity for fraction collection.

By knowing the portion of each of the isolated compounds diverted into the light scattering detector as compared to the portion directed to fraction collection, and by knowing the actual mass passing through the light scattering detector, it is then possible to calculate the total masses of each of the individual fraction collected compounds. Specifically, the total mass of any particular isolated compound which is fraction collected is determined by measuring the signal generated by the light scattering detector, (which is proportional to the total mass of the compound passing to the fraction collector), during the interval in time in which the compound is eluted and fraction collected, (as determined by the mass spectrometer). By knowing the correlation between the signal generated by the light scattering detector and the amount of mass passing therethrough and by knowing the portion of fluid sample diverted into the light scattering detector as compared to the remainder of the fluid sample which passes directly to the fraction collector microtiter plate, the amount of mass present in any of the various isolated fraction collected compounds is calculated.

Initially, a calibration curve between the mass passing through the evaporative light scattering detector and the signal generated by the evaporative light scattering detector is determined. Such a calibration curve can be established by determining the signal output when passing known masses through the light scattering detector.

An additional advantage of the present invention is that as the actual masses of the fraction collected compounds are known when these compounds are fraction collected in microtiter plates, the microtiter plate fraction collector can then itself later be concentrated by being dried down. Afterwards, it can be reconstituted to set point molarity based upon the weight of each isolated compound as determined by the light scattering detector. As such, the microtiter plate can itself be used to create daughter plates directly without any reformatting or weighing.

Furthermore, by performing real time mass determinations of fraction collected samples, the present invention can be used to automatically calculate the yield of a given reaction. Moreover, such mass determinations can also be used as a control function when fraction collecting such that a maximum amount of an isolated compound can be collected, with the remainder being diverted to a second fraction collector or to waste.

In addition, the present system can be adapted to perform simultaneous real time mass determinations of a plurality of fraction collected samples, wherein a plurality of simultaneously eluted fluid samples can be analyzed by the evaporative light scattering detector and the mass spectrometer. In various aspects of the invention, parallel simultaneously eluted fluid samples pass through a switching valve such that each of the samples can be analyzed by the evaporative light scattering detector and the mass spectrometer in turn. In alternate aspects, parallel light scattering detection is performed by a plurality of lasers or with a single laser having its beam sequentially directed towards the various samples eluted in parallel.

DESCRIPTION OF THE SPECIFIC EMBODIMENTS

Figure 1:
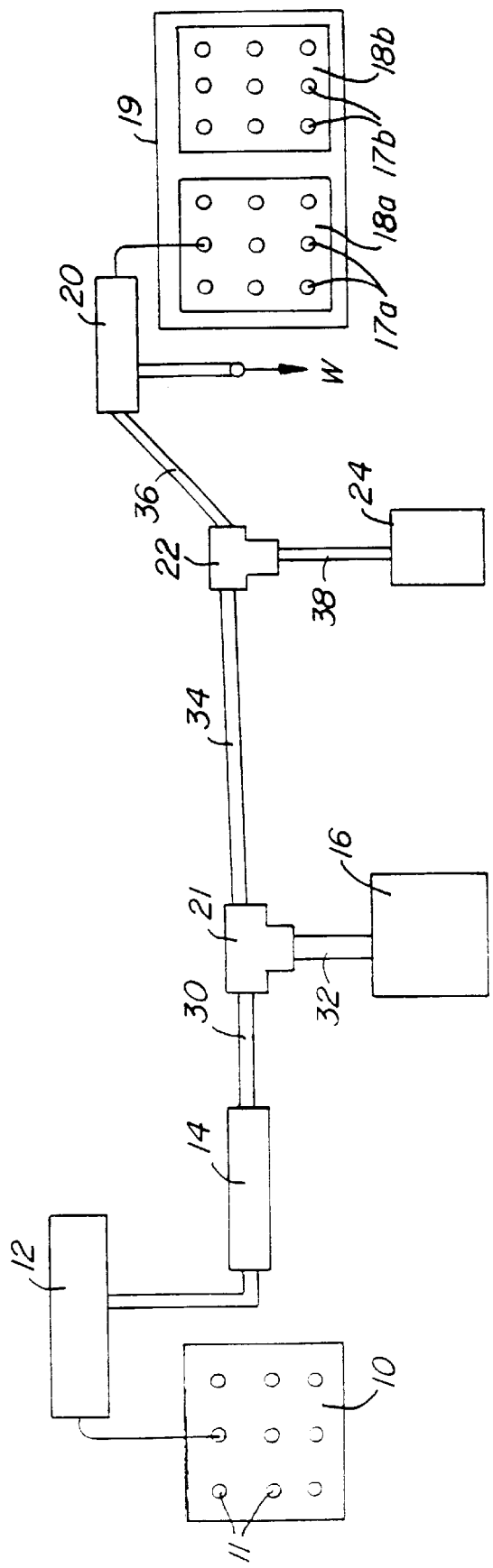
FIG. 1 is a schematic view of an apparatus for carrying out the present invention.

As seen schematically in FIG. 1, a plurality of chemical compounds can be synthesized or provided in microtiter plate format in reaction wells 11 of microtiter plate 10. A fluid handling robot 12, which may comprise a Gilson 215 Autosampler is adapted to draw up each of the fluid samples present in wells 11 of microtiter plate 10, and to sequentially load each of the fluid samples in wells 11 onto a fluid separation column 14.

Fluid separation column 14 may preferably comprise a high performance liquid chromatography (HPLC) column or a supercritical fluid (SFC) column composed of a solid sorbent material which operates to separate each of the component compounds in the fluid sample passing therethrough such that isolated compounds are sequentially eluted from the end of the column. Specifically, since each of the different component compounds found in each fluid sample will interact differently with the solid sorbent material contained within the separation column, each will accordingly take different amounts of time to pass through and be eluted out of the exit end of the column. Column 14 may preferably comprise a C18 Reverse Phase semi-preparatory or preparatory fluid separation column. Due to the small fluid samples used in the present microtiter plate format, the separation resolution achieved by the present semi-preparatory or preparatory fluid separation column approaches that of a standard smaller volume analytical column. It is to be understood, however, that fluid separation column 14 can be replaced by any form of fluid partitioning system.

After separated fluid is eluted from column 14, a very small portion, (typically on the order of 1%), is diverted through a splitter 21, (which may preferably comprise a Valco Tee), into mass spectrometer 16. Mass spectrometer 16 determines the molecular weights of the isolated compounds in the fluid sample passing sequentially therethrough and generates a signal corresponding to the molecular weights of the isolated compounds. Accordingly, mass spectrometer 16 identifies each of the isolated compounds passing sequentially therethrough on the basis of their respective molecular weights. When the signal from mass spectrometer 16 indicates a desired isolated compound is present in sufficient concentration, a liquid handling robot 20 is signaled to collect the desired compound in corresponding wells 17a of microtiter plate 18a of fraction collector 19. As illustrated, fraction collector 19 preferably comprises a plurality of microtiter plate collector racks (i.e.: individual microtiter plates shown here as 18a and 18b). Furthermore, it is to understood that liquid handling robot 20 could be replaced by a simple on/off valve or valving system.

When fraction collecting only a single compound from each of wells 11 in microtiter plate 10, a single microtiter plate 18a may be used. Preferably, the same spatial address is maintained between wells 11 in microtiter plate 10 and wells 17a in microtiter plate 18a when one isolated compound is fraction collected from each of the wells in microtiter plate 10. Alternatively, when more than one isolated compounds are to be fraction collected from any single well 11a in plate 10, a plurality of microtiter plates, (shown here as 18a and 18b), can be used such that first isolated compounds can be collected in wells 17a of microtiter plate 18a and second isolated compounds can be collected in wells 17b of microtiter plate 18b. It is to be understood that additional microtiter plates can be used as required when more than two compounds are fraction collected wells 11 of plate 10. Alternatively, a plurality of individual fraction collectors can be used for fraction collection. Using either a plurality of fraction collector racks (i.e.: microtiter plates) within a single fraction collector, or a plurality of separate fraction collectors, it is preferable to maintain the same spatial addresses among sample and fraction collection microtiter plate wells, with the number of fraction collection microtiter plates corresponding to the maximum number of different isolated compounds collected from any particular sample well. Accordingly, by using multiple microtiter plate fraction collectors, the same spatial addresses can be maintained for various isolated compounds fraction collected from a single sample well 11 in microtiter plate 10.

When used in conjunction with mass spectrometer 16, column 14 and fraction collector 18 can be used together to purify fluid samples by first separating a fluid sample into isolated compounds on column 14 and then collecting only desired compounds into fraction collector 18 on the basis of the signal output of mass spectrometer 16. Specifically, when desired compounds are not present in sufficient purity, or when undesirable compounds are eluted, (as indicated by the output signal of mass spectrometer 16), fraction collection is not performed, such that the non-desired portions of the fluid sample are conveniently expelled as waste W.

The amounts of flow diverted to splitters 21 and 22, and the volume of connecting tubes 32, 34 and 36, is set such that eluting compounds from column 14 reaches each of mass spectrometer 16, evaporative light scattering detector 24 and microtiter plate fraction collector 18 at the same time. Accordingly, at the moment in time when mass spectrometer 16 signals that fraction collection of a particular isolated compound reaching mass spectrometer 16 should commence, the same particular isolated compound will be reaching liquid handling robot 20 such that it can be diverted into fraction collector microtiter plate 18. Therefore, compound purification can be performed in real time.

A small portion, (typically on the order of 1%), of the separated fluid sample is diverted by splitter 22, (which preferably comprises a Valco Splitter Tee), towards an evaporative light scattering detector 24. Light scattering detector 24 measures the total mass of the fluid sample passing therethrough on the basis of the amount of light scattered per unit mass passing therethrough. An advantage of light scattering detection is that a signal which is mass dependent within a narrow range of response factors is produced. As such, the total mass of the fluid sample is determined without regard to the way in which various particles absorb light, which would in turn depend upon the structural nature of the particle, with different chromophores having a wide range of response factors, making system calibration difficult.

The signal generated by the light scattering detector will be in the form of an integer number of "area counts" which correspond to the mass of sample passing through the detector. Specifically, the area Counts are integrated to determine the mass of sample passing through the detector. As such, progressively larger masses passing through the detector generate greater numbers of area counts.

The actual total mass of any particular individual isolated compound which is fraction collected is determined by the mass passing through the light scattering detector during the interval of time during which fraction collection is performed. The mass passing through the light scattering detector represents a fixed portion (typically about 1%, depending upon the splitter arrangement used), of the mass passing into fraction collector 18 during the interval of time in which fraction collection is carried out. Accordingly, the total mass passing through the light detector is used to accurately determine the total mass of the fraction collected compound.

Preferably, prior to operation of the present system, a calibration curve is established for light scattering detector 24 by passing different known masses through the light scattering detector 24 and recording the number of area counts generated by the different known masses.

The particular isolated compound will reach light scattering detector 24 at the same time that it reaches mass spectrometer 16 and fraction collector microtiter plates 18. Accordingly, the signal generated by mass spectrometer 16 and light scattering detector 24 will correspond to the same particular isolated compound in the fluid sample.

Figure 2:
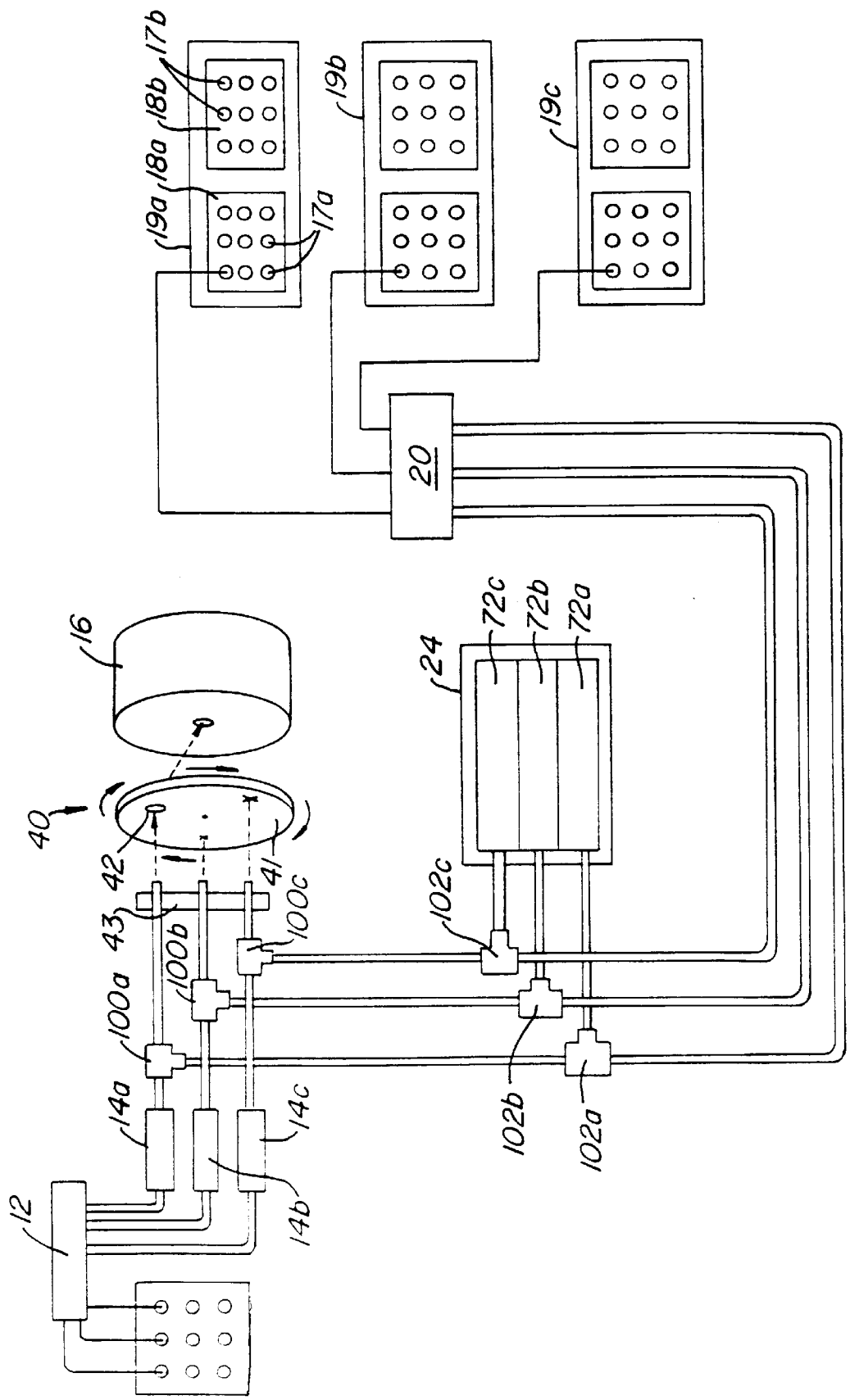
FIG. 2 is a schematic view corresponding to FIG. 1, but instead having parallel fluid columns and a selective electrospray blocking system for carrying out parallel fluid sample analysis.

Referring to FIG. 2, the present invention can be adapted for parallel evaporative light scattering detection such that a plurality of fluid separation columns 14a, 14b and 14c can be used at once. In such an arrangement, autosampler 12 loads different fluid samples onto a plurality of fluid columns 14a, 14b, 14c. Separated fluid samples are then simultaneously eluted from each of fluid columns 14a, 14b, 14c. A selective electrospray blocking system 40 rapidly selects between electrosprays of each of the simultaneously eluted fluid samples such that electrosprays of each of the separated fluid samples reach mass spectrometer 16 one after another. By rapidly selecting between each of the simultaneously eluted fluid samples, each of the isolated compounds present in the separated fluid samples can be detected.

In a preferred aspect, selective blocking system 40 comprises a rotating disc 41 having an off-center hole 42 passing therethrough and each of fluid columns 14a, 14b, and 14c are connected to a parallel channel electrosprayer 43 such that the fluid eluted from each of fluid columns 14a, 14b, and 14c is electrosprayed to pass in sequence through the hole 42 in rotating disc 41 as disc 41 is rotated. Specifically, parallel channel electrosprayer 43 preferably directs electrosprayed effluents from each of fluid columns 14a, 14b, and 14c towards locations which are equidistant from the center of the rotating disc and which are at a distance equal to the distance from the center of hole 42 to the center of rotating disc 41. An example of such a system is found in the Applicants' provisionally filed Application Serial No. 06/088,665, filed Jun. 9, 1998; and also in the Applicants' application entitled "Parallel Fluid Electrospray Mass Spectrometer", filed Nov. 3, 1998, the disclosure of both which are incorporated herein by reference in their entireties for all purposes.

Fluid splitters 100a, 100b and 100c, (which may preferably comprise Valco splitter Tees), divert the majority (typically 99%) of the separated fluid samples toward electrosprayer 24. Specifically, fluid splitters 102a, 102b and 102c, (which may also preferably comprise Valco splitter Tees), divert a small portion (typically 1%) of the separated fluid samples into electrosprayer 24, (which comprises parallel drift tubes 72a, 72b and 72c as will be explained). Fluid splitters 102a, 102b and 102c divert a majority, (typically 99%), of the separated fluid sample to liquid handling robot 20 for fraction collecting in fraction collectors 19a, 19b and 19c.

It is to be understood that any number of parallel fluid columns can be used, and that the present use of three fluid columns (14a, 14b, and 14c), is merely illustrative. It is also to be understood that any other form of switching valve system can be substituted for the present electrospray blocking system 40.

Figure 3:
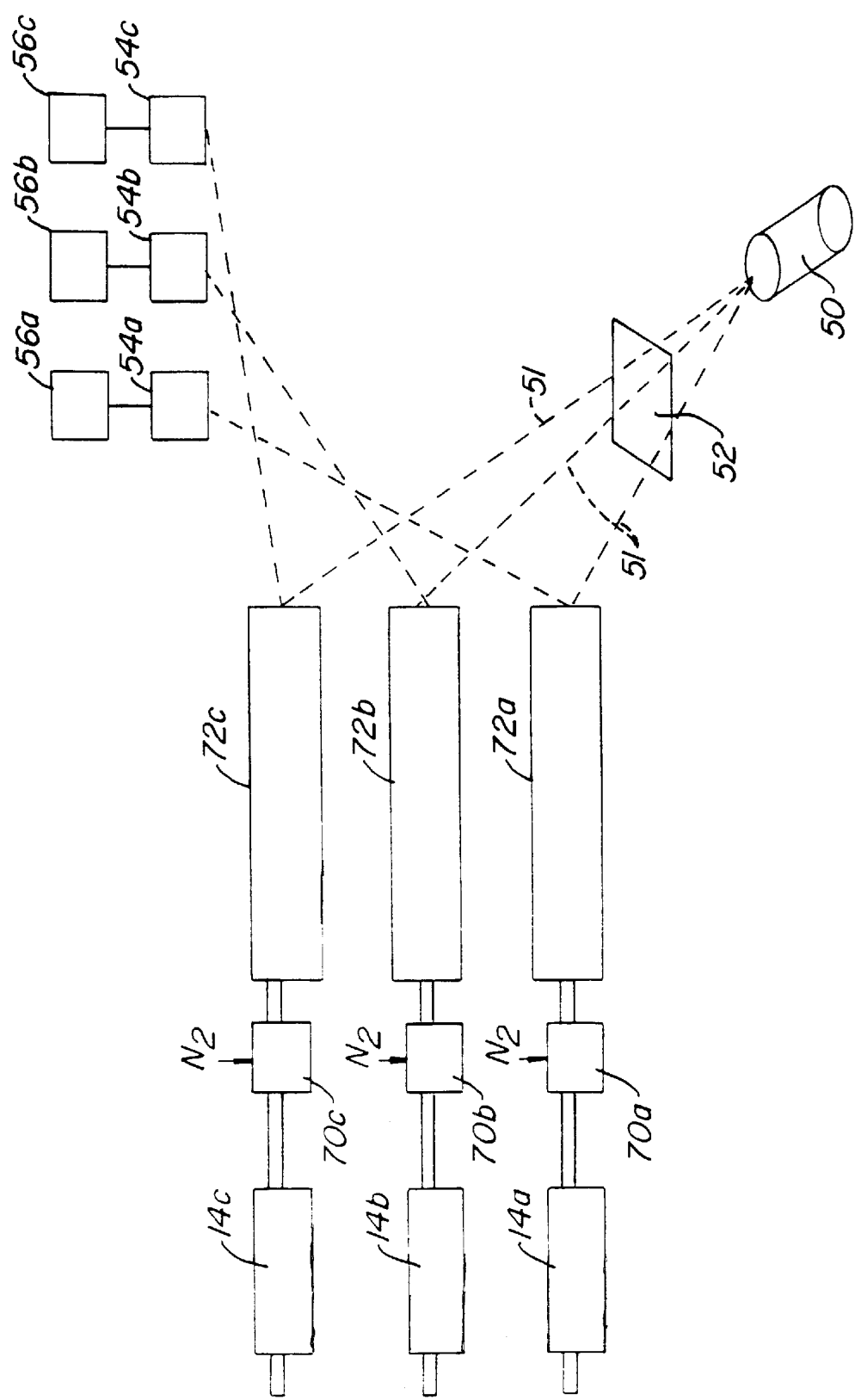
FIG. 3 is a schematic view of an alternate system for carrying out parallel evaporative light scattering detection comprising a movable scanning mirror and a single laser.

FIG. 3 shows a system for parallel light scattering detection in which fluid columns 14a, 14b and 14c simultaneously elute separated fluid samples which are separately and sequentially sampled by a laser light source, as follows. Nebulizers 70a, 70b and 70c are each connected to a nitrogen source. Nebulizers 70a, 70b and 70c cause the fluid samples sequentially eluted from each of fluid columns 14a, 14b and 14c to be passed as aerosol sprays along through drift tubes 72a, 72b and 72c, respectively. Laser 50 emits a beam 51 which is selectively directed towards the aerosol spray corresponding to the fluid eluted by each of the three fluid columns in sequence. Specifically, a beam selector 52, (which preferably comprises a movable scanning mirror) directs beam 51 from laser 50 in sequence toward the effluent of each of fluid columns 14a, 14b, and 14c. Laser beam 51 is scattered by each of the effluent streams and is received by photodetectors 54a, 54b and 54c, respectively, as the beam is scanned from fluid column 14a to 14b to 14c.

Each of photodetectors 54a, 54b and 54c, will preferably be operated together with a dedicated amplifier 56a, 56b and 56c. Accordingly, when laser beam 51 is directed towards each of the effluent streams, scattered light can be detected and amplified into a chromatographic signal. Rapid sequential sampling of each of the effluent streams provides an independent chromatograph for each column 14.

Figure 4:
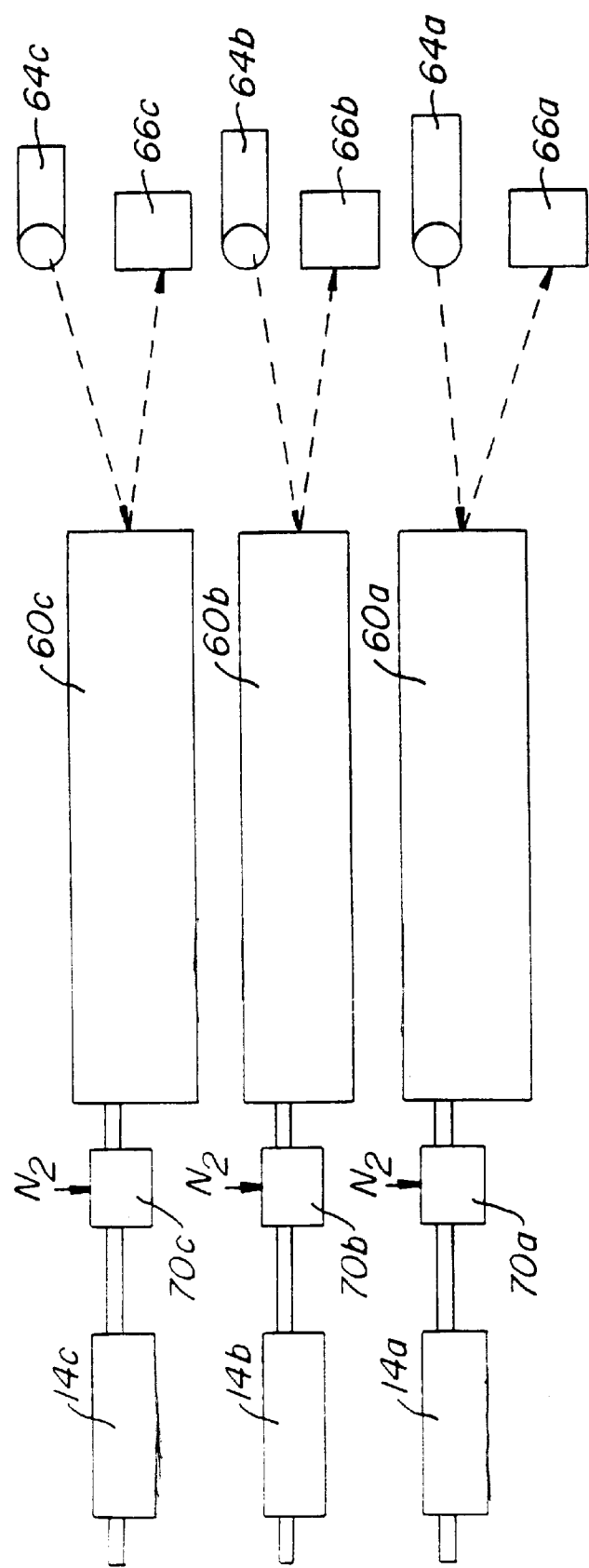
FIG. 4 is a schematic view of another alternate system for carrying out parallel evaporative light scattering detection comprising a plurality of lasers.

FIG. 4 shows another alternate system for parallel light scattering detection in which fluid columns 14a, 14b and 14c simultaneously elute separated fluid samples which are simultaneously sampled by separate laser light sources, as follows. In this arrangement, a plurality of separate drift tubes 60a, 60b and 60c, each having dedicated light sources 64a, 64b, 64c ; and photomultipliers 66a, 66b and 66c are used.

The ability to perform parallel evaporative light scattering detection, (i.e.: to perform evaporative light scattering detection on a plurality of separated fluid samples at the same time), provides very high throughput quantitation of the masses of the isolated compounds present in a plurality of fluid samples.

What is claimed is:

1. Method for measuring the masses of compounds present in a fluid sample during fraction collection, comprising:

separating the fluid sample into sequentially eluted isolated compounds by passing the fluid sample through a fluid separation device, diverting a first portion of the sequentially eluted isolated compounds into a mass spectrometer, thereby determining the molecular weight of each isolated compound in sequence;

diverting a second portion of the sequentially eluted isolated compounds into an evaporative light scattering detector, thereby determining the total masses of each isolated compound passing therethrough in sequence;

fraction collecting at least one of the isolated compounds into a fraction collector; and calculating the total masses of the isolated compounds in the fraction collector during fraction collection on the basis of the second portion of each isolated compound diverted into the evaporative light scattering detector during a period of fraction collection.

2. The method of claim 1, further comprising, purifying at least one of the isolated compound by fraction collecting when a desired concentration of the at least one isolated compound is present in the fluid sample as determined by the mass spectrometer.

3. The method of claim 1, wherein passing the fluid sample through a fluid separation device comprises, passing the fluid sample through a liquid chromatography fluid column.

4. The method of claim 1, wherein passing the fluid sample through a fluid separation device comprises, passing the fluid sample through a supercritical fluid column.

5. The method of claim 3 or 4, wherein passing the fluid sample through the fluid column, comprises, passing the fluid sample through a preparatory or semi-preparatory fluid column.

6. The method of claim 1, wherein fraction collecting the isolated compounds into a fraction collector comprises, fraction collecting into at least one microtiter plate.

7. The method of claim 1, further comprising, extracting the fluid sample from a plurality of fluid samples in a microtiter plate and loading the fluid sample onto the fluid separation device with a liquid handling robot.

8. The method of claim 1, wherein the evaporative light scattering detector comprises a plurality of parallel drift tubes.

9. The method of claim 8, wherein the evaporative light scattering detector further comprises a plurality of lasers, with each laser being positioned to simultaneously direct a laser beam toward one of the plurality of parallel drift tubes.

10. The method of claim 8, wherein the evaporative light scattering detector further comprises a laser and a scanning mirror, wherein the laser and scanning mirror are positioned to direct a laser beam toward one of the plurality of parallel drift tubes in sequence.

* * * * *